(12) United States Patent
Chang (10) Patent No.: US 10,947,199 B2
(45) Date of Patent: Mar. 16, 2021

(54) SPIRO AND CYCLIC BIS-BENZYLIDENE PROTEASOME INHIBITOR FOR THE TREATMENT OF CANCER, DIABETES AND NEUROLOGICAL DISORDERS

(71) Applicant: UP THERAPEUTICS, INC., Elkridge, MD (US)

(72) Inventor: Yung-Nien Chang, Elkridge, MD (US)

(73) Assignee: UP THERAPEUTICS, INC., Elkridge, MD (US)

( * ) Notice: Subject to any disclaimer, the term of this patent is extended or adjusted under 35 U.S.C. 154(b) by 0 days.

(21) Appl. No.: 16/481,562

(22) PCT Filed: Jan. 30, 2018

(86) PCT No.: PCT/US2018/015826
§ 371 (c)(1),
(2) Date: Jul. 29, 2019

(87) PCT Pub. No.: WO2018/140907
PCT Pub. Date: Aug. 2, 2018

(65) Prior Publication Data
US 2019/0365726 A1  Dec. 5, 2019

Related U.S. Application Data (60) Provisional application No. 62/451,920, filed on Jan. 30, 2017.

(51) Int. Cl.
| | |
|---|---|
| *C07D 221/20* | (2006.01) |
| *A61K 31/397* | (2006.01) |
| *A61K 31/403* | (2006.01) |
| *A61K 31/438* | (2006.01) |
| *C07D 205/12* | (2006.01) |
| *C07D 209/54* | (2006.01) |

(52) U.S. Cl.
CPC .......... *C07D 221/20* (2013.01); *A61K 31/397* (2013.01); *A61K 31/403* (2013.01); *A61K 31/438* (2013.01); *C07D 205/12* (2013.01); *C07D 209/54* (2013.01)

(58) Field of Classification Search
None
See application file for complete search history.

(56) References Cited

U.S. PATENT DOCUMENTS

| | | |
|---|---|---|
| 2013/0079370 A1 | 3/2013 | Brnjic et al. |
| 2014/0370528 A1 | 12/2014 | Brnjic et al. |
| 2016/0106725 A1 | 4/2016 | Roden et al. |

OTHER PUBLICATIONS

Nencioni. Leukemia, 2007, 21, 30-36 (Year: 2007).*
LV. Inorganic Chemistry, 2010, 49, 6628-35 (Year: 2010).*
Wang, X., et al., "The 19S Deubiquitinase Inhibitor b-AP15 Is Enriches in Cells and Elicits Rapid Commitment to Cell Death," Mol. Pharmacol. 2014;85(6):932-945.
International Search Report and Written Opinion for PCT Patent App. No. PCT/US2018/015826 (dated May 3, 2018).
International Preliminary Report on Patentability for PCT Patent App. No. PCT/US2018/015826 (dated Jul. 30, 2019).
Carreira, E. M., et al., "Four-Membered Ring-Containing Spirocycles: Synthetic Strategies and Opportunities," Chem. Rem. 2014;114(16):8257-8322.
Search Report and Written Opinion from Singapore Patent App. No. 11201907844T (dated Dec. 11, 2020).
Extended European Search Report for European Patent App. No. 18744809.7 (dated Jan. 15, 2021).
Soliman, A. M., et al., "Evaluation of Antiproliferative Potency and Induced Biochemical Parameters of Novel Pyridine Derivative Against Leukemia, Lung, Breast and Colon Cancer Cell Lines," World Journal of Pharmaceutical Research 2015;4(8):100-115.
El-Hussieny, M., et al., "Chemistry of Phosphorous Ylides Part 42: Reaction of Dipyridyl Ethanedione with Phosphorus Reagents. Cytotoxic Activity of Phosphanylidene-Cyclobutane, Oxaphosphetane, and Pyridazinone," Phosphorus, Sulfur, and Silicon and The Related Elements 2015;190(11):1845-1856.
Zou, Q., et al., "Effective Two-Photon Photodynamic Therapy of Xenograft Tumors Sensitized by Water-Soluble Bis (arylidene)cycloalkanone Photosensitizers," J. Med. Chem. 2015;58(20):7949-7958.
Zou, Q., et al., "Polyethylene glycol-functionalized bis(arylidene)cycloalkanone photosensitizers for two-photon excited photodynamic therapy," Proceedings of SPIE, Dec. 11, 2012, vol. 8553, p. 8553.

* cited by examiner

*Primary Examiner* — Noble E Jarrell
(74) *Attorney, Agent, or Firm* — Cermak Nakajima & McGowan LLP; Malcolm K. McGowan (57) ABSTRACT

Described herein are spiro and cyclic bis-benzylidine proteasome inhibitors, which inhibit the proteasome function through either ubiquitin receptor ADRM1/RPN13 or proteasome DUB enzymes (USP14, UCH37 and RPN11), and which can be used for the treatment of cancers/diabetes/neurological disorders.

7 Claims, 11 Drawing Sheets

SPIRO AND CYCLIC BIS-BENZYLIDENE PROTEASOME INHIBITOR FOR THE TREATMENT OF CANCER, DIABETES AND NEUROLOGICAL DISORDERS

CROSS-REFERENCE TO RELATED APPLICATIONS

This application is a national stage entry under 35 USC 371 of PCT/US2018/015826, filed Jan. 30, 2018, which claims priority from U.S. Provisional Application 62/451,920, filed Jan. 30, 2017.

BACKGROUND

Ubiquitin-Proteasome System (UPS) play a vital role in cellular homeostasis, cell cycle progression and signaling pathways that are altered in many diseases. Modulating UPS function with small molecules that directly bind to the proteasomal proteins can be useful to treat wide variety of diseases specifically cancers, diabetes and neurological disorders. Targeting the aberrant metabolism of cancer cells is an emerging approach for cancer therapy. Indeed, despite early skepticism that inhibiting protein degradation with a proteasome inhibitor would provide a sufficient therapeutic index for cancer therapy, over the last decade three proteasome inhibitors that target the catalytic function of the 20S proteasome were approved by FDA to treat multiple myeloma and mantle cell lymphoma. However, their limited efficacy against solid tumors, toxicities and the emergence of resistant multiple myeloma has driven search for alternative proteasome inhibitors with distinct and complementary mechanisms of action.

SUMMARY

Provided herein are spiro and cyclic bis-benzylidine small molecules (Up I, II and III, Up compounds hereafter), a new type of proteasome inhibitor, that inhibit the proteasome function through either ubiquitin receptor ADRM1/RPN13 or proteasome DUB enzymes (USP14, UCH37 and RPN11) can be used for the treatment of cancers/diabetes/neurological disorders. The Up compounds bind to the 19S regulatory particle of the proteasome which triggers a rapid and toxic accumulation of high molecular weight poly-ubiqutinated protein aggregates, reflecting inhibition of deubiquitinase activity and substrate recognition by the proteasome.

DETAILED DESCRIPTION

Provided herein are compounds having the structure of formula either I, or II, or III, or IV, shown below wherein each pair of A is one of:
(i) phenyl, optionally substituted with 1-5 substituents selected from the group consisting of R1, OR1, NR1R2, S(O)qR1, SO$_2$NR1R2, NR1SO$_2$R2, C(O)R1, C(O)OR1, C(O)NR1R2, NR1C(O)R2, NR1C(O)OR2, CF$_3$, and OCF$_3$;
(ii) naphthyl, optionally substituted with 1-5 substituents selected from the consisting of R1, OR1, NR1R2, S(O)qR1, SO$_2$NR1R2, NR1SO$_2$R2, C(O)R1, C(O)OR1, C(O)NR1R2, NR1C(O)R2, NR1C(O)OR2, CF$_3$, and OCF$_3$;

(iii) a 5 or 6 membered monocyclic heteroaryl group, having 1-3 heteroatoms selected from the group consisting of 0, N, and S, optionally substituted with 1-3 substituents selected from the group consisting of R1, OR1, NR1R2, S(O)qR1, SO$_2$NR1R2, NR1SO$_2$R2, C(O)R1, C(O)OR1, C(O)NR1R2, NR1C(O)R2, NR1C(O)OR2, CF$_3$, and OCF$_3$; and (iv) an 8 to 10 membered bicyclic heteroallyl group containing 1-3 heteroatoms selected from the group consisting of 0, N, and S; and the second ring is fused to the first ring using 3 to 4 carbon atoms, and the bicyclic hetero aryl group is optionally substituted with 1-3 substituents selected from the group consisting of R1, OR1, NR1R2, S(O)qR1, SO$_2$NR1R2, NR1SO$_2$R2, C(O)R1, C(O)OR1, C(O)NR1R2, NR1C(O)R2, NR1C(O)OR2, CF$_3$, and OCF$_3$;

(v) any group belongs to R1 or R2 wherein n represents number of atoms ranging from 0-4 (0, 1, 2, 3, 4) and can be a Carbon, Nitrogen or Oxygen. In the case of nitrogen, it can be NH, NR1 or NR2;

wherein X is Hydrogen, OR1 or NP, wherein P is selected from the group consisting of R1, C(O)R1, C(O)OR1, C(O)NR1R2, S—N(R1)COOR1, and S—N(R1), wherein Y is selected from the group consisting of O, S, NR1 and CR1R2, and wherein R1 and R2 are selected from the group consisting of hydrogen, nitro, hydroxyl, carboxy, amino, halogen, cyano and C1-C14 linear or branched alkyl groups, that are optionally substituted with 1-3 substituents selected from the group consisting of Ci-C4 linear or branched alkyl, up to perhalo substituted C1-C14 linear or branched alkyl, Ci-Ci4 alkoxy, hydrogen, nitro, hydroxyl, carboxy, amino, C1-C14 alkylamino, C-i-C-n dialkylamino, halogen, and cyano;

wherein Z is selected from the group consisting of hydrogen; C1 to C14 linear, branched, or cyclic alkyls; alkenyls, phenyl; benzyl; 1-5 substituted benzyl, Ci to C3 alkyl-phenyl, wherein the alkyl moiety is optionally substituted with halogen up to perhalo; up to perhalo substituted C1 to C14 linear or branched alkyls; —(CH2)q-K, where K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N and S, wherein said alkyl moiety is optionally substituted with halogen up to perhalo, and wherein the variable q is an integer ranging from 0 to 4;

wherein B is (i) R1, C(O)R1, C(O)OR1, C(O)NR1R2, S—N(R)COOR1, S—N(R1)COO(B), S(B); and wherein each R1-R2, other than perhalo substituted C1-C14 linear or branched alkyl, is optionally substituted with 1-3 substituents independently selected from the group consisting of C-1-C14 linear or branched alkyl, up to perhalo substituted C1-C14 linear or branched alkyl, C1-C3 alkoxy, hydroxyl, carboxy, amino, C1-C3 alkylamino, C1-C6 dialkylamino, halogen, cyano; and where in R$_3$ is H, C$_{1-6}$-alkyl, C$_{2-6}$-alkenyl; C$_{1-3}$-alkoxy-C$_{1-6}$-alkyl-; C$_{1-3}$-alkoxy-C$_{2-6}$-alkenyl-; aryl-C$_{0-6}$-alkykheteroaryl-C$_{0-6}$-alkyl-; heterocyclyl-C$_{0-6}$-alkyl-; cycloalkyl-C$_{0-6}$-alkyl-; —C$_{1-6}$-alkyl-COOC$_{1-6}$-alkyl; —C$_{2-6}$-alkyl-aryloxy; C$_{1-6}$-alkyl-heteroaryl; C$_{1-6}$-alkyl-heterocyclyl; C$_{1-6}$-alkyl-cycloalkyl; C$_{1-6}$-alkyl-aryl; COR$^4$, where R$^4$ is selected from: C$_{1-6}$-alkyl; C$_{2-6}$-alkenyl; C$_{1-6}$-alkoxy; C$_{1-3}$-alkoxy-C$_{1-6}$-alkyl-; C$_{1-3}$-alkoxy-C$_{2-6}$-alkenyl-; aryl-C$_{0-6}$-alkyl-; heteroaryl-C$_{0-6}$-alkyl-;heterocyclyl-C$_{0-6}$-alkyl-;cycloalkyl-C$_{0-6}$-alkyl-; —C$_{1-6}$-alkyl-COOC$_{1-6}$-alkyl; NH$_2$; —NHC$_{1-6}$-alkyl; —N(C$_{1-6}$-alkyl)$_2$; —C$_{0-6}$-alkyl-aryloxy.

The compounds described herein bind to proteasomal proteins as either DUB inhibitor or proteasome receptor inhibitor.

Also provided herein is a method of inhibiting proteasomes in a mammal by administering an effective amount of the compound disclosed herein to the mammal. As used herein, the term "mammal" includes, for example, humans, dogs, and cats.

Also provided herein are methods of treating a disease in a mammal by administering to the mammal a therapeutically effective dose of a compound as described herein. The disease to be treated may be, for example, cancer, or diabetes, or neurological disorders.

The compounds disclosed herein may be usefully administered alone or in combination with at least one other therapeutic agent or radiation, as can be determined by a medical professional.

Exemplary compounds which meet the requirements described herein include the following:

C$_{22}$H$_{19}$N$_3$O$_5$
Mol. Wt.: 405.4

C$_{25}$H$_{21}$N$_3$O$_5$
Mol. Wt.: 459.45

C$_{34}$H$_{30}$N$_4$O$_7$
Mol. Wt.: 606.62

C₃₁H₂₉ClN₄O₆
Mol. Wt.: 589.04

C₃₃H₂₉ClN₄O₇
Mol. Wt.: 629.06

C₂₃H₁₅Cl₄NO₂
Exact Mass: 476.99
Mol. Wt.: 479.18

C₂₀H₁₃Cl₄NO
Exact Mass: 422.98
Mol. Wt.: 425.14

Up109

Up117

Up161

Up200

-continued

Up111

EXAMPLES

Example 1: Inhibition of Cancer Cell Proliferation and Colony Formation by Up Therapeutics Compounds (Up Compounds)

Treatment of cancer cells with Up compounds inhibited cell proliferation as indicated by MTT assay. Briefly cancer cells incubated with Up compounds for the period of 24 or 48 or 72 hours and the cell viability was measured using MTT assay. IC50 of compounds listed in Table1. Also Up109 and Up117 also significantly blocked colony formation in OV2008 and A2780 cancer cells corresponding to their IC50 values. Both compounds were similarly active in SKOV3 and its taxol resistant line (SKOV3-TR) whereas Taxol show 7-fold difference.

TABLE 1

IC50 values of selected Up Therapeutics compounds (in μM)

| Name | Cell Line Type | Up101 | Up109 | Up117 |
|---|---|---|---|---|
| MM.1S | Multiple Myeloma | | 0.035 | 0.042 |
| RPMI8226 | Multiple Myeloma | | 0.123 | 0.14 |
| RPMI8226-R | Multiple Myeloma | | 0.061 | 0.078 |
| LNCaP | Prostate Cancer | | 0.065 | 0.087 |
| PC-3 | Prostate Cancer | | 0.057 | 0.074 |
| DU145 | Prostate Cancer | | 0.077 | 0.13 |
| ES2 | Ovarian Cancer | 0.453 | 0.022 | 0.041 |
| OVCAR3 | Ovarian Cancer | 0.761 | 0.021 | |
| OVCAR5 | Ovarian Cancer | 0.592 | 0.019 | 0.037 |
| SKOV3 | Ovarian Cancer | >1.25 | 0.045 | 0.157 |
| SKOV3-TR | Ovarian Cancer | >1.25 | 0.058 | 0.202 |
| A2780 | Ovarian Cancer | 0.365 | 0.013 | 0.022 |
| OV2008 | Ovarian Cancer | 0.968 | 0.034 | 0.047 |
| HS578T | Triple Negative Breast Cancer | | 0.017 | 0.032 |
| MDA-MB-231 | Triple Negative Breast Cancer | | 0.038 | 0.056 |
| HCC1806 | Triple Negative Breast Cancer | | 0.042 | 0.071 |
| HeLa | Cervical Cancer | | 0.075 | 0.089 |
| HepG2 | Liver Cancer | | 0.118 | 0.447 |
| HFF(primary human foreskin fibroblast) | Normal Cell line | >1.25 | >1.25 | >1.25 |

Example 2

Figure 1:
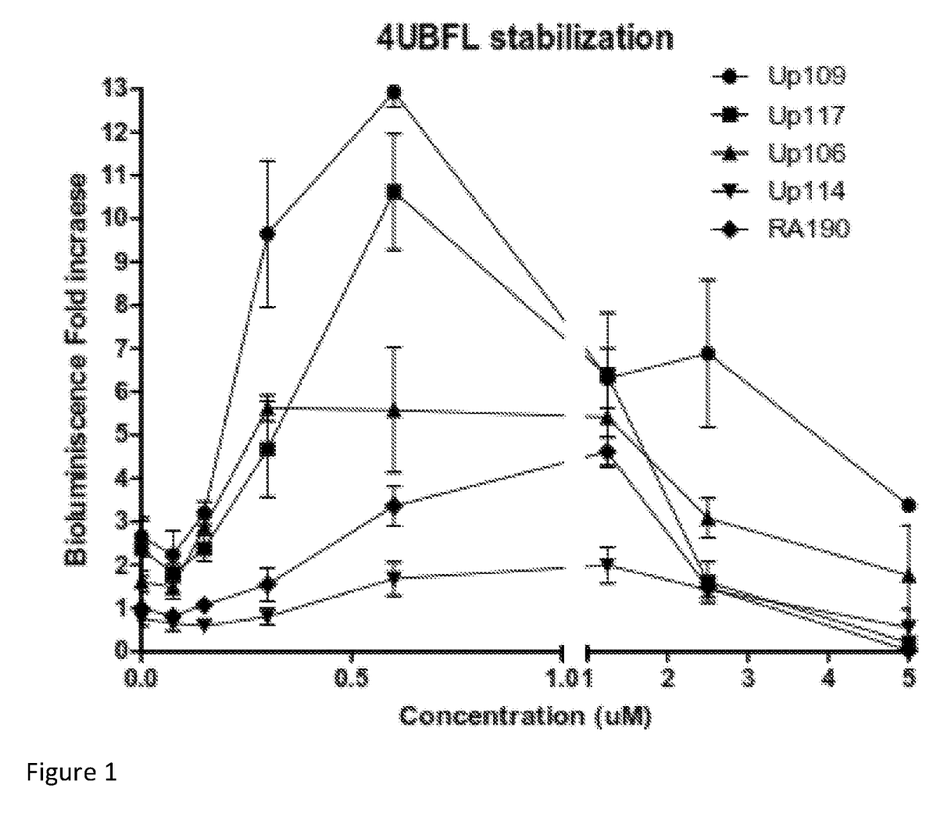
FIG. 1: Up109 and Up117 stabilized proteasome-targeted firefly luciferase reporter.

To measure proteasome function in live cells, we utilized an engineered ubiquitin-firefly (4Ub-FL) reporter in which four copies of mutant ubiquitin (ubiquitin G76V) gene are fused to the N-terminus of the firefly luciferase (FL) gene. The results of this experiment, shown in FIG. 1, reveal that the 4Ub-FL reporter protein is rapidly degraded by the proteasome. Importantly, treatment of 293TT cells expressing 4Ub-FL gene with proteasome inhibitors results in its stabilization and an increase in luciferase activity. Interestingly, treatment of Up109 and Up117 produced a greater increase in the 4Ub-FL bioluminescence than RA190 in a dose dependent manner. Up109 shows thirteen-fold increase in bioluminescence whereas eleven and fivefold increase was observed with Up117 and RA190 respectively compared to before treatment.

Example 3

Figure 2:
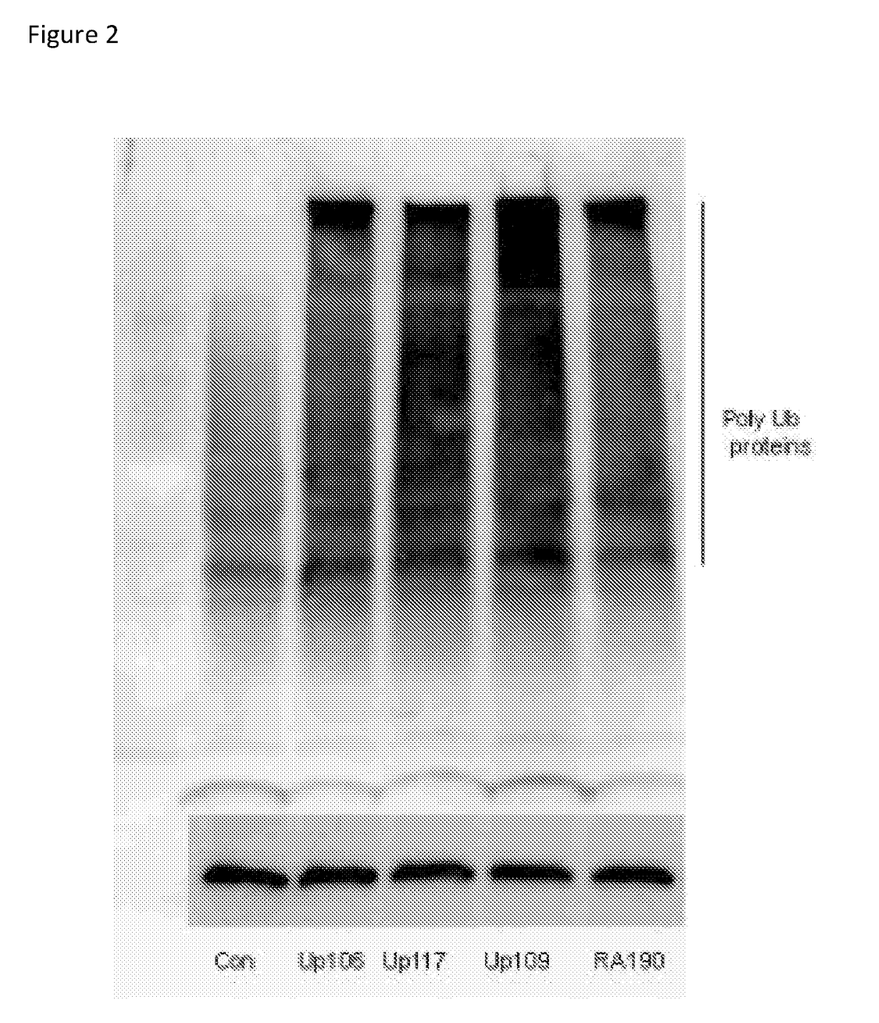
FIG. 2: Up109 and Up117 accumulated poly ubiquitin tagged proteins.

Accumulation of poly ubiquitinated proteins is a general phenomenon of proteasome inhibition. We examined the impact of these compounds on the levels of polyubiquitinated proteins in HeLa cells by anti-K48-linked ubiquitin immunoblot analysis. The results of this experiment, shown in FIG. 2, reveal that treatment of HeLa cells with Up109 or Up117 (4 hr) dramatically increased the levels of K48-linked polyubiquitinated proteins similarly to RA190. However, accumulated K48 polyubiquitinated proteins observed following exposure to compounds exhibited a higher molecular weight than that seen in Bortezomib-treated cells and occurred more rapidly. These results suggest that the toxicity exerted by Up109 and Up117 in cervical cancer cells is associated with a prior accumulation of high-molecular-weight polyubiquitinated proteins and occurs by a mechanism distinct to Bortezomib.

Example 4

Figure 3:
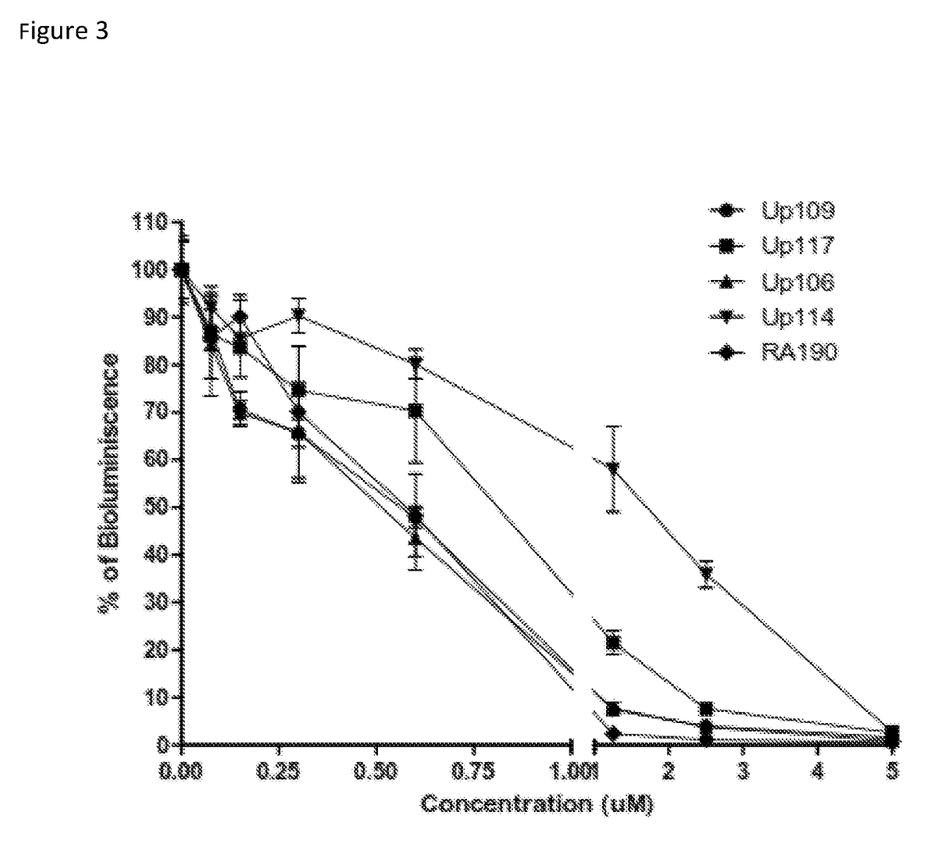
FIG. 3: Up109 and Up117 inhibited NFκB signaling.

NFκB is constitutively activated in many cancers including high grade cervical intraepithelial neoplasia (CIN) and cervical cancer. Stimulation of 293 cells carrying an NFκB reporter construct with human TNF-a leads to increased reporter activity, and Up109, UP117 and RA190 produced a significant dose-dependent decrease of reporter activity after stimulation with TNF-a (FIG. 3). Stabilization of IkB-a was observed in HeLa cells post treatment with Up109 and Up117 in the presence of TNF-a.

Example 5

Figure 4:
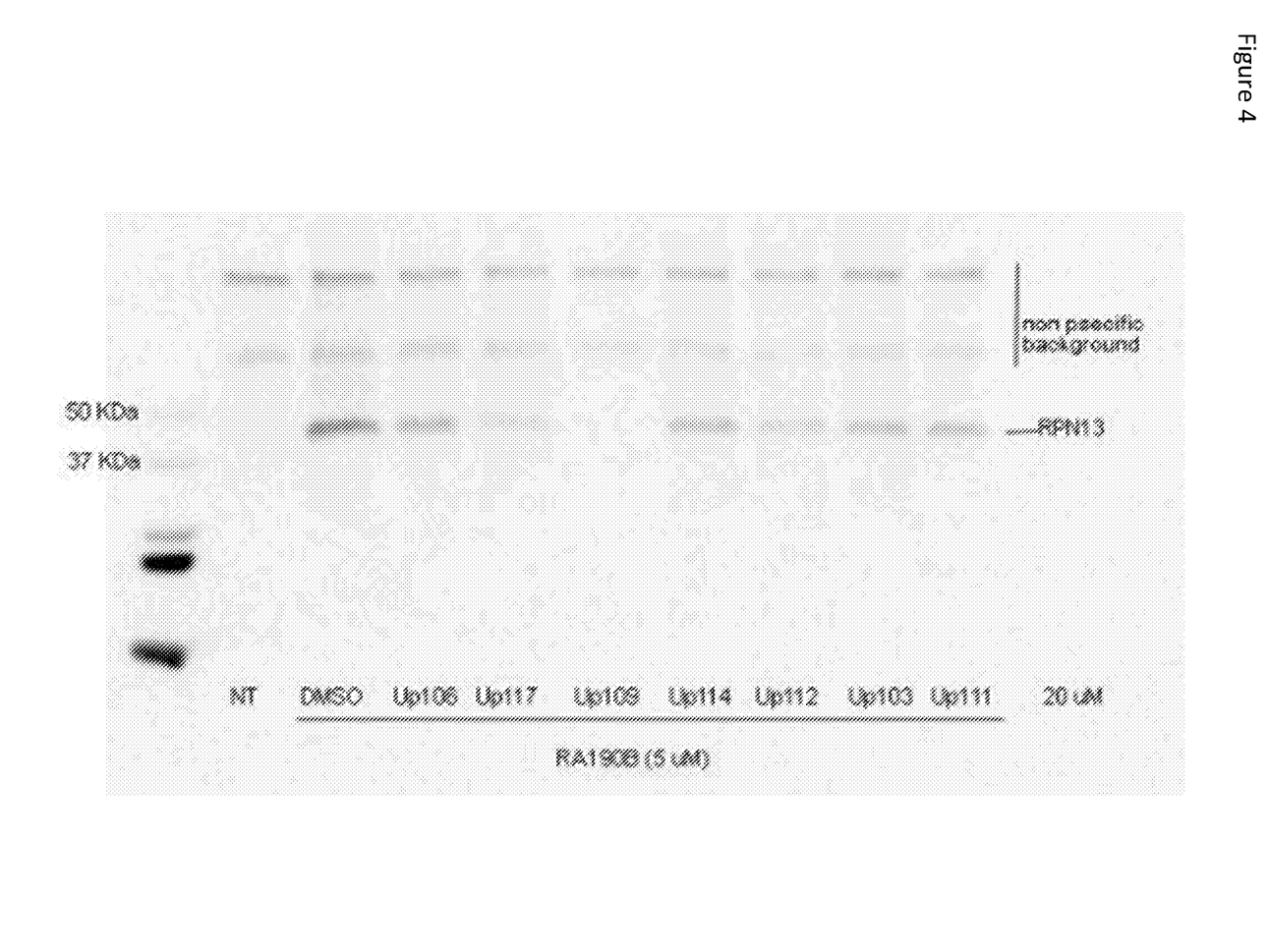
FIG. 4: Up109 and Up117 binds to RPN13.

To identify the cellular target, a competition assay was performed using RA190B probe. Earlier we showed that biotinylated RA190 (RA190B) covalently binds to RPN13. We used RA190B as a probe to determine the Up compound binding to RPN13. HeLa cell lysate was pretreated with Up109 or Up117 and then subsequently treated with RA190B. Lysate was denatured under reduced conditions and proteins were separated on a gel and probed with HRPStreptavidin. FIG. 4 shows that disappearance of RA190B labeling of the 42 kDa protein in the presence of Up109 and UP117 indicates competition with RA190B for binding to RPN13.

Example 6: Up Compounds Accumulated Poly Ubiquinated Proteins In Vitro

Figure 5:
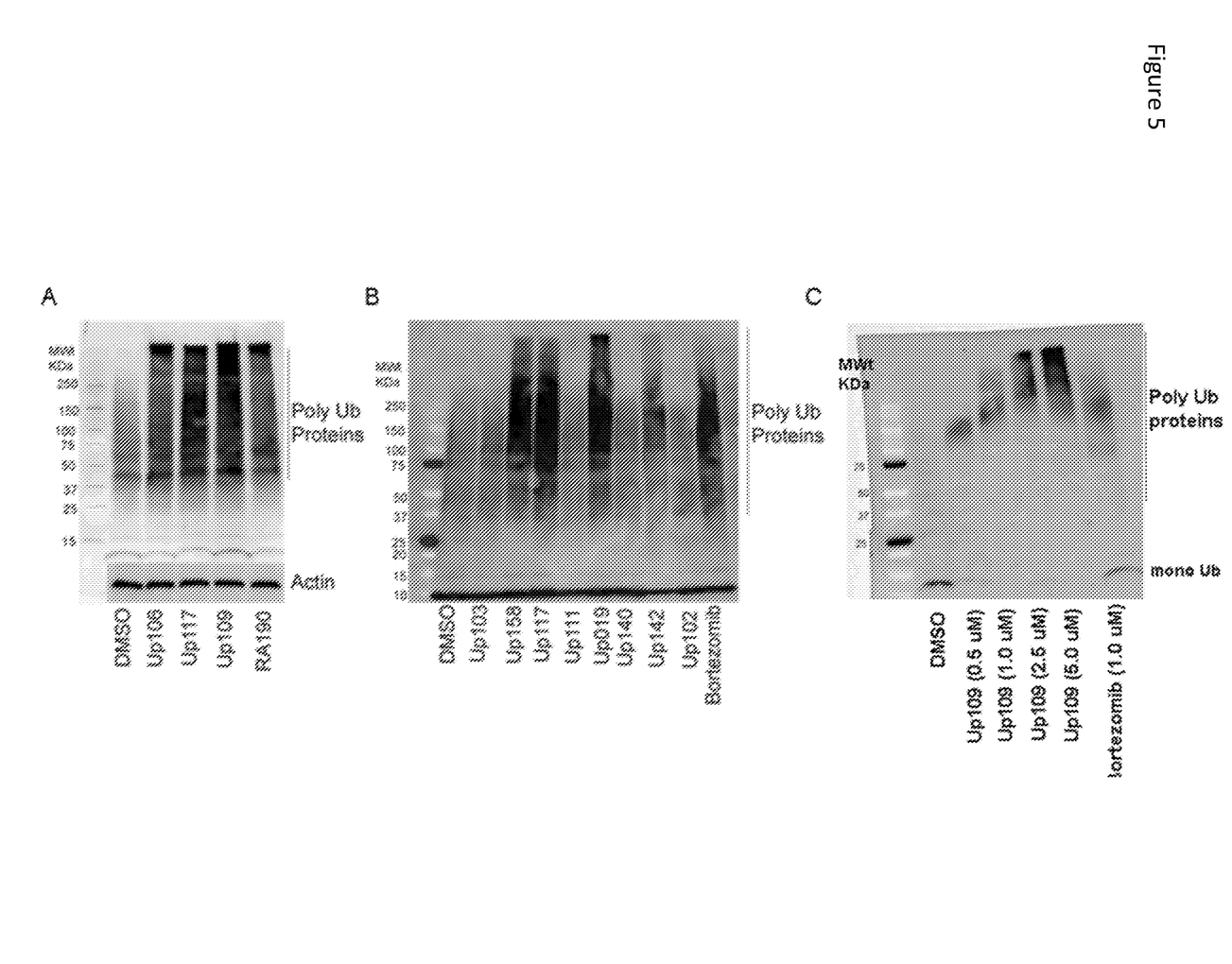
FIG. 5: Accumulation of PolyUB proteins with the treatment of Up compounds: (A) HeLa cells treated with Up compounds (1 μM) for 4 h and immunoblotted with K48 linked anti-Ub antibody; (B) OV2008 cells treated with Up compounds (1 μM) for 12 h and immunoblotted with anti-Ub antibody; (C) LNCaP cells treated with Up compounds for 4 h and immunoblotted with anti-Ub antibody.

Accumulation of poly ubiquitinated proteins is a general phenomenon of proteasome inhibition. We examined the impact of these compounds on the levels of polyubiquitinated proteins cancer cells by anti-ubiquitin immunoblot analysis. Cancer cell lines (HeLa, OV2008 and LNCaP) treated with Up compounds for the period of indicated time and the cells were lysed and subjected to Western blot Analysis. Immunoblot with anti-Ubiqutin antibody show the accumulation of polyUbiquitinated proteins in treated cells (FIG. 5). HeLa cells were probed with K48-linked anti-Ub antibody which recognizes the proteins tagged with ubiqiuitin through K-48 linkage. K48-linked polyubiquitin chains attached to substrate proteins often serve as a recognition sequence for targeting and destruction of the substrate by the 26S Proteasome, OV2008 and LNCaP cells were probed with anti-Ub antibody.

Example 7: Up109 Stabilized Proteasome Dependent Reporter Protein

Figure 6:
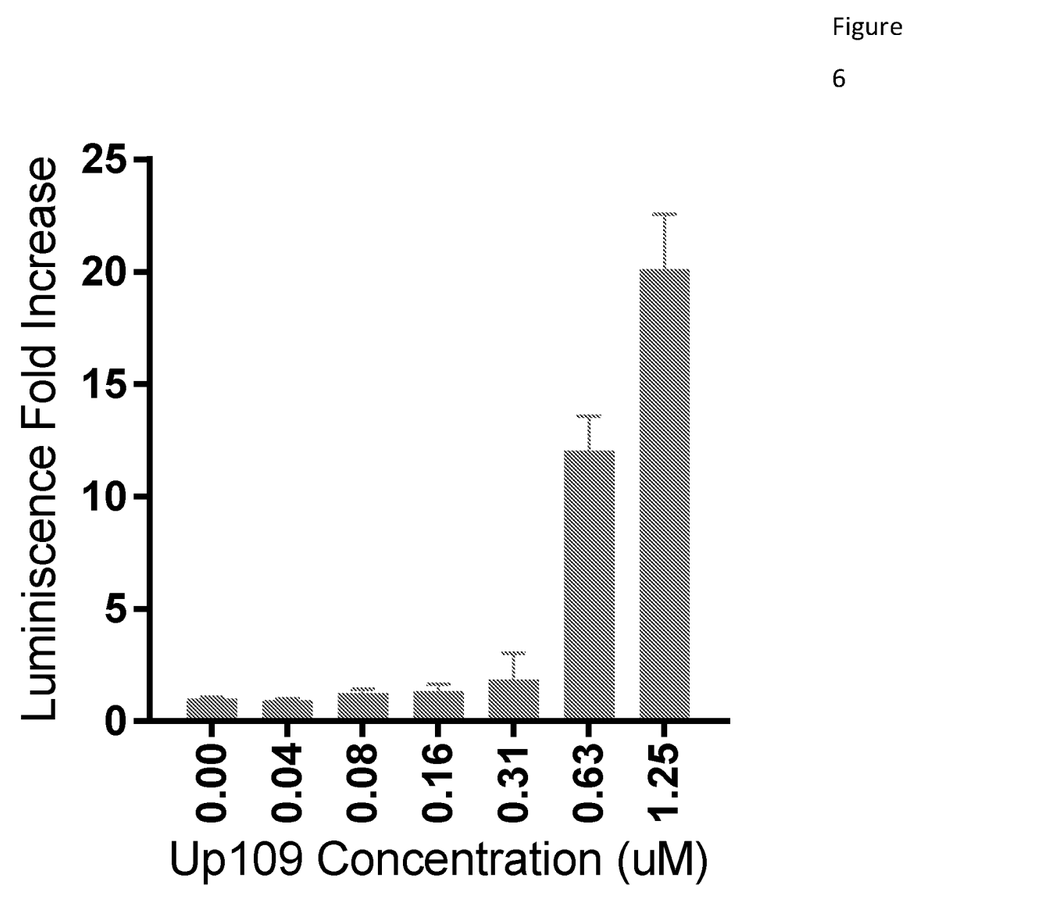
FIG. 6: Stabilization of 4UBFL reporter protein with Up109 treatment.

To measure proteasome function in live cells, we utilized an engineered ubiquitin-firefly (4Ub-FL) reporter in which four copies of mutant ubiquitin (ubiquitin G76V) gene are fused to the N-terminus of the firefly luciferase (FL) gene. The 4Ub-FL reporter protein is rapidly degraded by the proteasome (FIG. 6). Importantly, treatment of 293TT cells expressing 4Ub-FL gene with Up109 results in its stabilization and an increase in luciferase activity. Treatment of Up109 produced a greater increase in the 4Ub-FL bioluminescence in a dose dependent manner.

Example 8: Up109 and Up117 Binds to RPN13

Figure 7:
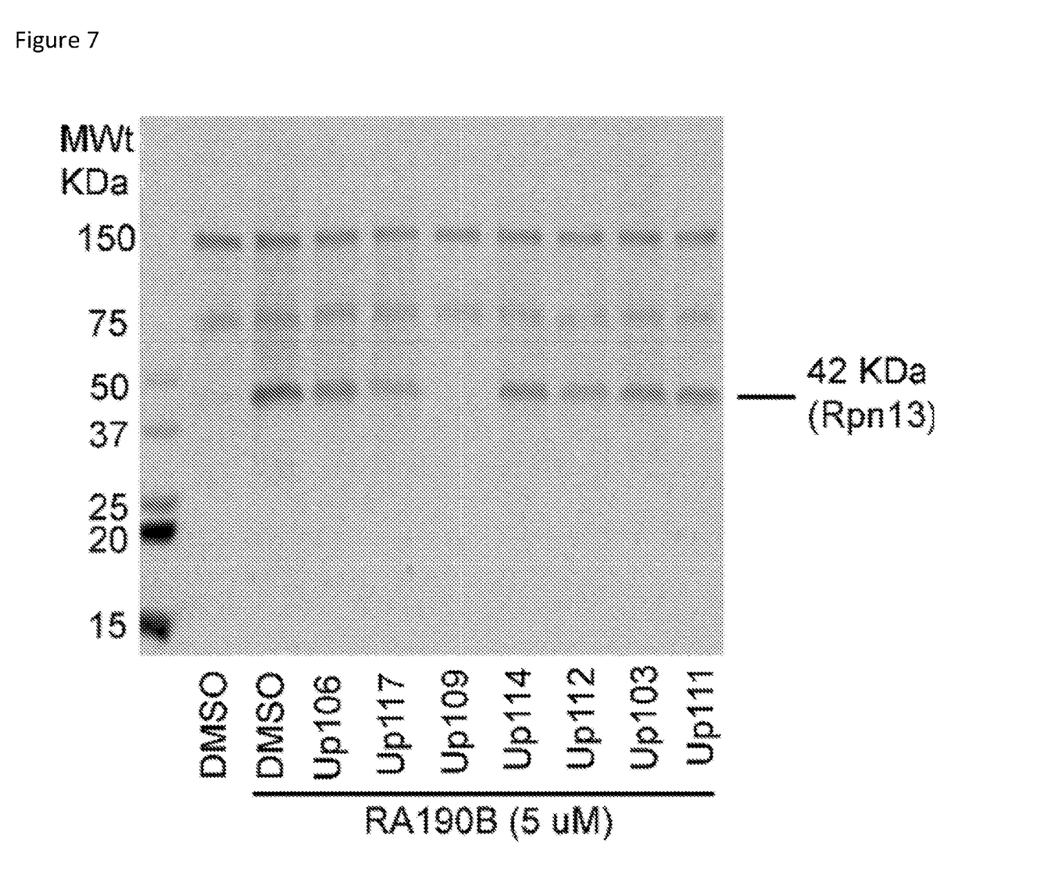
FIG. 7: Up109 binds to RPN13.

To identify the cellular target, a competition assay was performed using RA190B probe. Earlier we showed that biotinylated RA190 (RA190B) covalently binds to RPN13. We used RA190B as a probe to determine the Up compounds binding to RPN13. OV2008 cell lysate was pretreated with Up compounds (25 µM) and then subsequently treated with RA190B (5 µM). Lysate was denatured under reduced conditions and proteins were separated on a gel and probed with HRP Streptavidin. Disappearance of RA190B labeling of the RPN13 protein in the presence of Up109 and UP117 indicates competition with RA190B for binding to RPN13 (FIG. 7).

Example 9: Up109 Elevated ER Stress and Apoptosis

Figure 8:
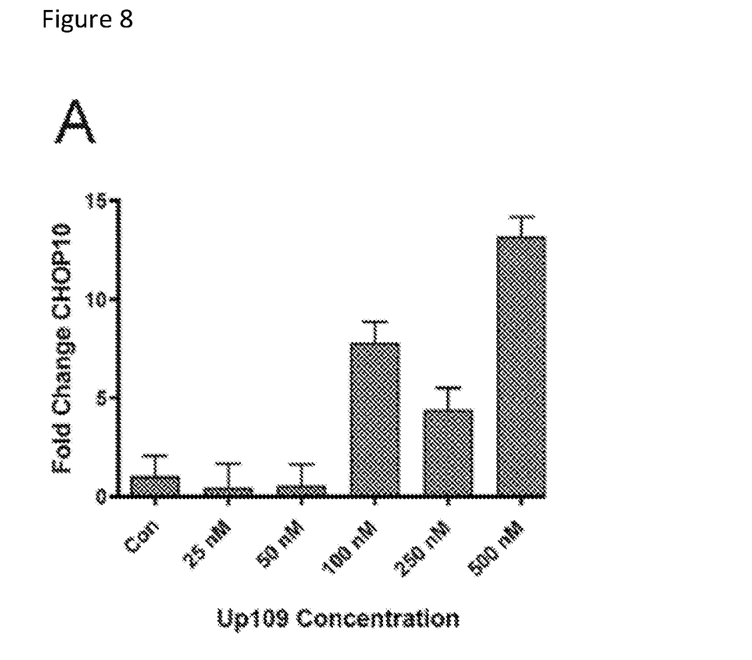
FIG. 8: (A) CHOP-10 quantification in ES2 cells treated with Up109 for 12 h; (B) Annexin-V staining by FACS analysis of ES2 cells treated with Up109 and Bortezomib for 12 h.

Accumulation of unfolded proteins upon the inhibition of proteasome function rapidly induces endoplasmic reticulum (ER) stress. ER stress triggers an evolutionarily conserved series of signal-transduction events, which constitute the unfolded protein response (UPR). The UPR attempts to restore protein homeostasis by eliminating the accumulated unfolded proteins in the ER; however, if protein homeostasis cannot be restored, apoptosis is triggered. C/EBP homologous protein (CHOP) is elevated at the onset of UPR-induced programmed cell death. Up109 treatment of ES2 cells rapidly up-regulated CHOP-10 mRNA expression (FIG. 8A). Annexin-V positive cells indicate the elevation of apoptosis by Up109 treatment (FIG. 8B).

Example 10: Up109 Stabilized 4UBFL In Vivo

Figure 9:
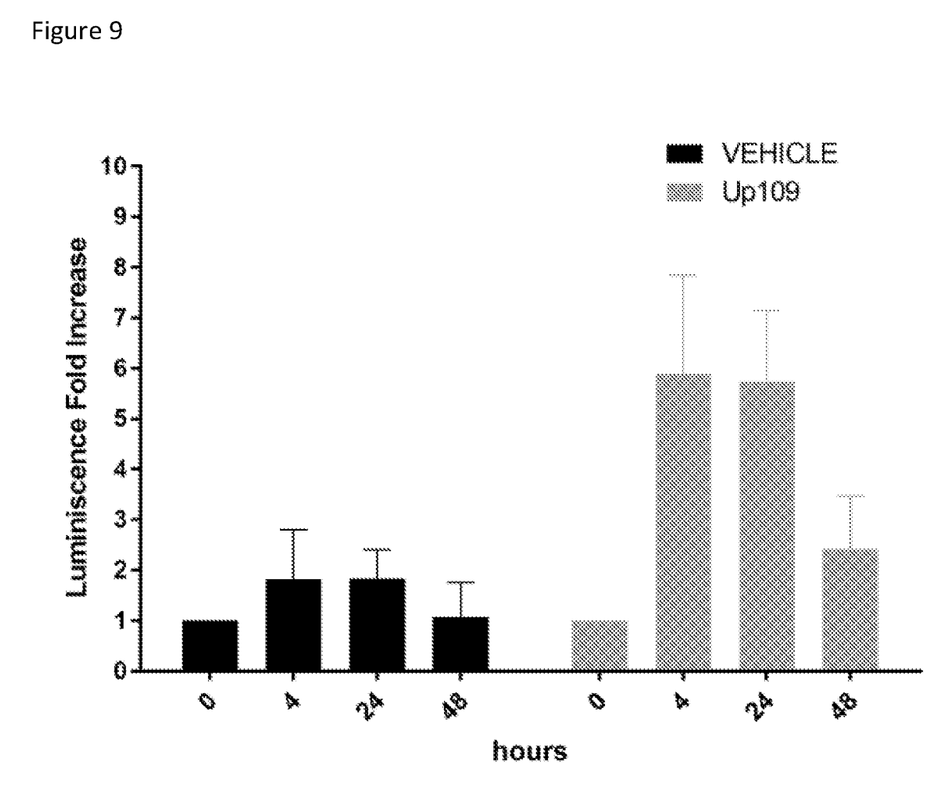
FIG. 9: BALB/C mice were electroporated with 4UBFL gene and treated with Up109 and the IVIS imaging was used to quantify luciferase activity.

To test for proteasome inhibition by Up109 in vivo, muscle cells of live Balb/c mice transduced with the 4UbFL reporter DNA construct by electroporation. After i.p. injection of luciferin, the enzymic activity of luciferase in the transfected muscle tissue was visualized as bioluminescence using an IVIS imager. At two days post electroporation of the 4UbFL DNA, mice were imaged and base line luminescence recorded. The control group (n=5) of mice was treated i.p. with vehicle alone and another group (n=5) treated i.p with Up109 (40 mg/Kg). After 4 h, 24 h and 48 h post treatment mice were again imaged and luminescence was quantified (FIG. 9). This result indicates (1) Up109 has good accessibility to solid tissue; (2) Up109 could potentially be dosed every other day.

Example 11: Dose Limiting Toxicity Studies

To identify the optimal dose that induces a clinical effect and operates with acceptable toxicity a set of experiments has been performed on female Balb/C strain mice with Up109. Individual groups of mice (n=3) were injected i.p. with increasing single doses of Up109 (3, 10, 20, 40 and 100 mg/Kg) and the endpoint evaluations included clinical observations and body weights. No clinically apparent sign of adverse effect was found with Up109. Another experiment was done with repeated i.p. doses of Up109 (40 mg/Kg, n=5) every other day for two weeks. No observable toxicities/weight loss were found.

Example 12: In Vivo Efficacy of Up109 Against ES2 Ovarian Tumor Growth

Figure 10:
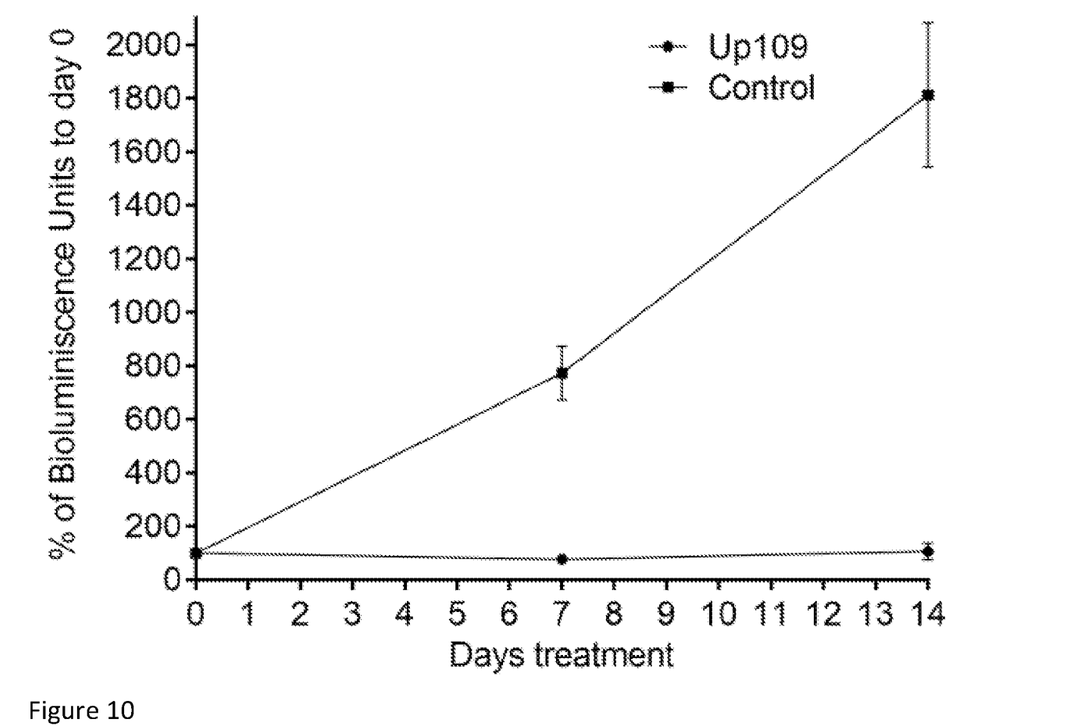
FIG. 10: In vivo efficacy of Up109 against ES2Lu tumor growth.

To test the efficacy of Up109 to treat the human ovarian cancer ES2 xenograft model, the luciferase-expressing ES2 cells (ES2-Lu) were inoculated into peritoneal cavity of nude female mice (i.e. orthotopically). Two days after inoculation the mice were imaged for their basal luminescence activity and then randomized into two groups (n=10). First group was treated with the vehicle and the second group was treated with Up109 (10 mg/Kg) on alternate days for two weeks. Mice were imaged after the first and second week of treatment for their luciferase activity. As indicated in FIG. 6, Up109 significantly reduced the tumor burden compared to the vehicle and there was no weight loss and any observable side effects. Tumor burden in the vehicle group mice was excessive and sacrificed at the end of the treatment (FIG. 10).

Example 13: Up Compounds General Synthetic Scheme

Reaction conditions: (a) substituted aldehydes, NaOH, Ethanol; (b) 4M HCl in dioxane; (c) acid chloride, DCM, triethyl amine or acid, HOBt, HBTU, DMF, DIPEA; (d) alkyl bromide, acetone, $K_2CO_3$; (e) sulfonyl chloride, DCM, triethyl amine. R = different substituents on the aromatic ring.

What is claimed is:

1. A compound selected from the group consisting of:

and

2. A compound according to claim 1 which binds to proteasomal proteins as either DUB inhibitor or proteasome receptor inhibitor.

3. A method of inhibiting proteasomes in a mammal by administering to the mammal an effective amount of the compound of claim 1.

4. A method of treating multiple myeloma, prostate cancer, ovarian cancer, triple negative breast cancer, cervical cancer, or liver cancer in a mammal by administering to the mammal a therapeutically effective dose of the compound of claim 1.

5. The method of claim 4 wherein the mammal is a human, or a dog, or a cat.

6. The method of claim 4 wherein the compound of claim 1 is administered alone or in combination with at least one other therapeutic agent or radiation.

7. The compound according to claim 1, wherein the compound has the formula